US008113316B2

(12) United States Patent
Sward et al.

(10) Patent No.: US 8,113,316 B2
(45) Date of Patent: Feb. 14, 2012

(54) SCAFFOLDING AND WORKTABLE APPARATUS

(76) Inventors: Kurt Sward, Deerfield, IL (US); Rick Ellison, Chicago, IL (US); Brian Clemens, Geneva, IL (US); Peter Tennessen, Chicago, IL (US); Austen He, Chicago, IL (US)

(*) Notice: Subject to any disclaimer, the term of this patent is extended or adjusted under 35 U.S.C. 154(b) by 816 days.

(21) Appl. No.: 11/745,894

(22) Filed: May 8, 2007

(65) Prior Publication Data

US 2007/0261916 A1 Nov. 15, 2007

Related U.S. Application Data (60) Provisional application No. 60/746,716, filed on May 8, 2006.

(51) Int. Cl.
*E04G 1/32* (2006.01)
(52) U.S. Cl. ........... 182/222; 182/152; 182/155; 108/62
(58) Field of Classification Search .................. 182/222, 182/223, 119, 152, 153, 25, 129; 108/11, 108/13, 115, 116, 126, 130, 129, 62
See application file for complete search history.

(56) References Cited

U.S. PATENT DOCUMENTS

| 1,774,268 | A | * | 8/1930 | Harding | 182/223 |
| 1,975,595 | A | * | 10/1934 | Wadkins | 108/14 |
| 2,633,395 | A | * | 3/1953 | Zenner | 108/62 |
| 2,956,849 | A | * | 10/1960 | Dow | 108/14 |
| 4,951,780 | A | * | 8/1990 | Kim | 182/27 |
| 4,951,781 | A | * | 8/1990 | Bliss | 182/152 |
| 4,995,611 | A | * | 2/1991 | Goldthorpe | 273/123 R |
| 5,190,303 | A | * | 3/1993 | Schumacher et al. | 280/38 |
| 5,332,062 | A | * | 7/1994 | Revere | 182/27 |
| 5,711,400 | A | * | 1/1998 | Tan | 182/119 |
| 6,712,180 | B2 | * | 3/2004 | Levy | 182/153 |
| 6,892,860 | B2 | * | 5/2005 | Gibson et al. | 182/222 |
| 7,516,704 | B2 | * | 4/2009 | Snider et al. | 108/25 |
| 2004/0238278 | A1 | * | 12/2004 | Gibson et al. | 182/129 |
| 2004/0238280 | A1 | * | 12/2004 | Gibson et al. | 182/153 |

* cited by examiner

*Primary Examiner* — Katherine Mitchell
*Assistant Examiner* — Daniel Cahn
(74) *Attorney, Agent, or Firm* — Vedder Price P.C.

(57) ABSTRACT

The present disclosure relates to a scaffolding and worktable apparatus with pivotally connected end legs, and in particular, to an apparatus that can be modified from a scaffold to a worktable by rotating collapsible end legs from a first position to a second position and an apparatus that can also be stored or used in a flattened configuration by rotating the end legs to a third stored position.

11 Claims, 9 Drawing Sheets

SCAFFOLDING AND WORKTABLE APPARATUS

REFERENCE TO RELATED APPLICATION

The present patent application claims priority from and the benefit of U.S. Provisional Patent Application No. 60/746,716, filed May 8, 2006, and entitled SCAFFOLDING AND WORKTABLE APPARATUS, which prior application is hereby incorporated herein by reference.

FIELD OF THE DISCLOSURE

The present disclosure relates to a scaffolding and worktable apparatus with pivotally connected end legs, and in particular, to an apparatus that can be modified from a scaffold to a worktable by rotating collapsible end legs from a first position to a second position and that can also be stored or used in a flattened configuration by rotating the end legs to a third position.

BACKGROUND OF THE INVENTION

Tools and equipment are often needed to enhance a human's capacity to accomplish physical tasks. These objects are used by laborers at construction worksites, by home owners during condo renovations, by car mechanics in their trade, by military personnel on maneuvers, etc. Recent developments in tools and equipment design directs designers to evolve monofunctional objects into multipurpose objects. Kitchen utensils gain functions, and plastic bags for the storage of food in cold environments are now designed to withstand heating in a microwave oven, etc. This evolutionary tendency faces numerous limitations and obstacles for which inventive steps are needed.

First, functions must be complimentary and useful for each trade and for each new item and must be based on a plurality of parameters. Amongst the myriad of possible key combinations, effective concepts result only rarely and after much inventive effort toward a proper new embodiment that advances the tool and equipment industry. Second, the union of multiple functions often results in a loss of efficiency or efficacy of the primary function of the object. For example, the multipurpose nature of a Swiss army knife, while useful in varied circumstances where weight and encumbrance is not primary (e.g., camping), is in fact not an adequate tool on a worksite because each of its functions has been limited somewhat by the grouping of multiple functions in one tool. Inventors struggle with weight, cost impact, size, and a wide variety of challenges associated with the design of a multipurpose tool or multipurpose equipment.

Worksites are often cluttered with tools and equipment. Safety concerns are raised when a worker must work among so much equipment. By reducing the number of tools and pieces of equipment needed to perform a task, safety is improved and the work process is optimized. In some circumstances, workers need worktables and small scaffolds at the same worksite. Scaffoldings are temporary frameworks made of wood, pipes, or other materials used to support people and materials in the construction or repair of buildings. Workbenches are table-size devices used in woodworking, metalworking, or other trades where a horizontal surface is required. Most workbenches are 3 to 4 feet high and are designed for use at a height where tasks such as sawing, cutting, or glueing are performed comfortably by most workers. What is needed is a multipurpose structure capable of serving as both a workbench and a scaffold at a desired location without undue effort.

SUMMARY

The present disclosure relates to a scaffolding and worktable apparatus with pivotally connected end legs, and in particular, to an apparatus that can be modified from a scaffold to a worktable by rotating collapsible end legs from a first position to a second position and that can also be stored or used in a flattened configuration by rotating the end legs to a third position.

BRIEF DESCRIPTION OF THE DRAWINGS

Certain embodiments are shown in the drawings. However, it is understood that the present disclosure is not limited to the arrangements and instrumentality shown in the attached drawings.

DETAILED DESCRIPTION

For the purposes of promoting and understanding the principles disclosed herein, reference is now made to the preferred embodiments illustrated in the drawings, and specific language is used to describe the same. It is nevertheless understood that no limitation of the scope is thereby intended. Such alterations and further modifications in the illustrated devices and such further applications of the principles disclosed and illustrated herein are contemplated as would normally occur to one skilled in the art to which this disclosure relates.

Figure 1:
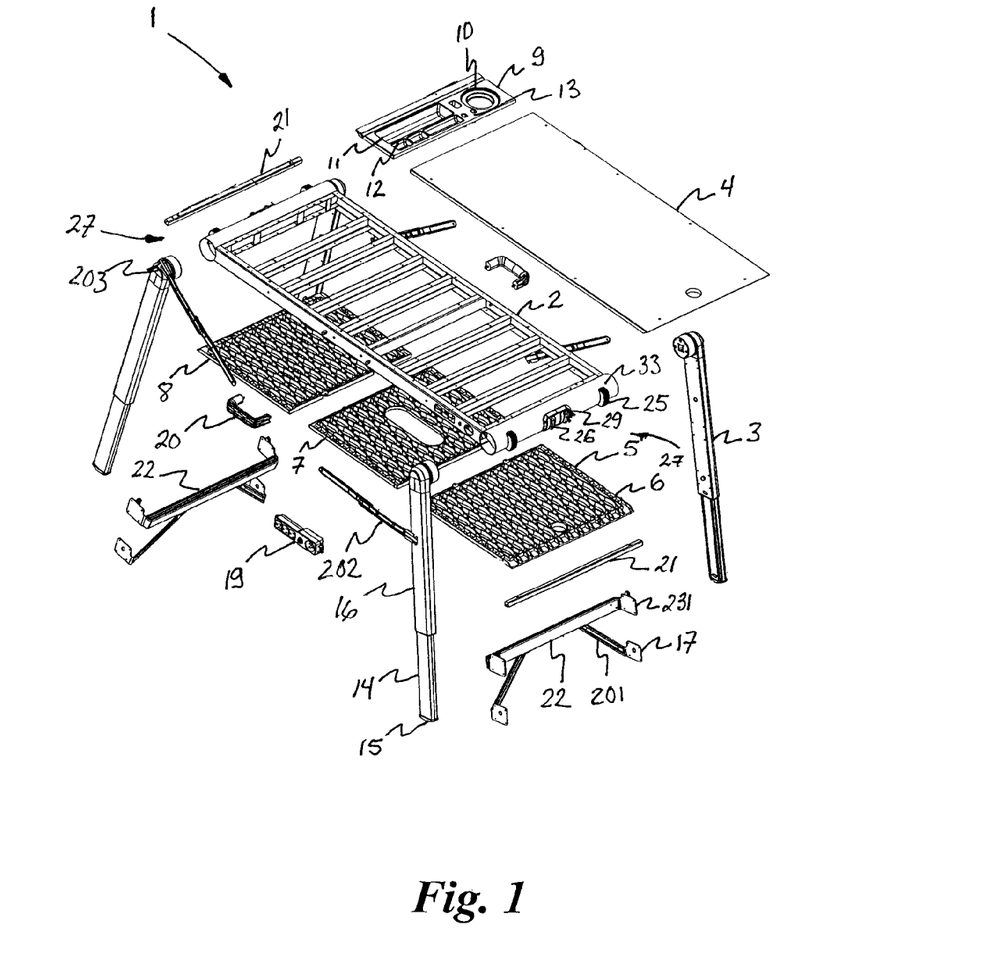
FIG. 1 is an isometric exploded view of the scaffolding and worktable apparatus according to an embodiment of the present disclosure.
Figure 2A:
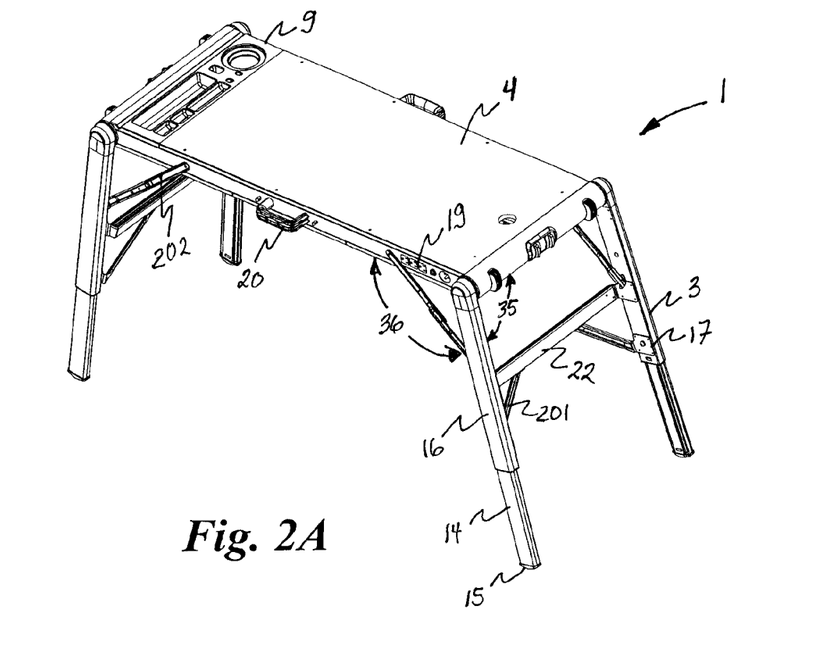
FIG. 2A is an isometric view of the scaffolding and worktable apparatus in the worktable configuration according to an embodiment of the present disclosure.
Figure 2B:
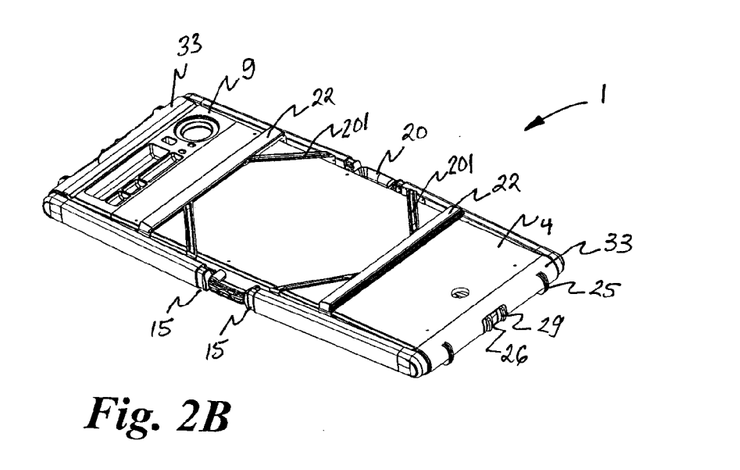
FIG. 2B is an isometric view of the scaffolding and worktable apparatus in the stored configuration according to an embodiment of the present disclosure.
Figure 2C:
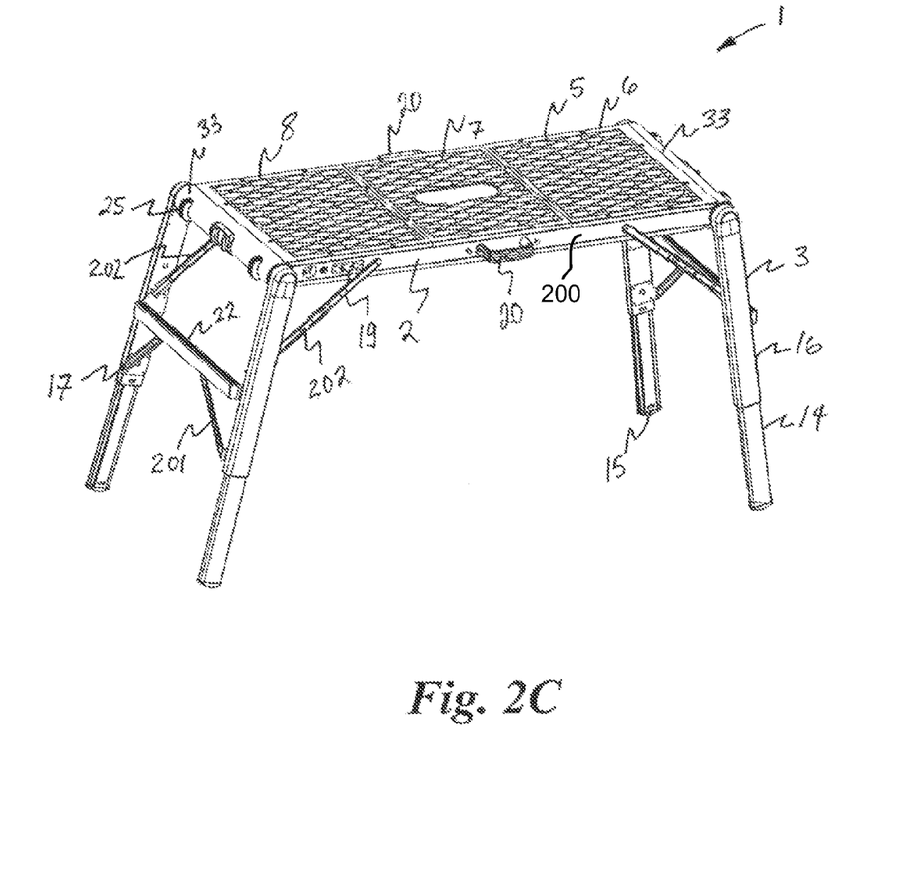
FIG. 2C is an isometric view of the scaffolding and worktable apparatus in the scaffolding configuration according to an embodiment of the present disclosure.

The present disclosure is a detailed description of one possible contemplated embodiment. FIG. 1 is a isometric exploded view of the scaffolding and worktable apparatus 1. The apparatus 1 is made of a platform 2 comprising at least a worktable surface 4 and a scaffolding surface 5 with at least one end piece 33. The apparatus also comprises at least one leg 3 pivotally connected to the end piece 33 and a locking mechanism 27 (not shown in FIG. 1 but found inside the end piece 33) for securing the at least one leg 3 in a series of at least three positions as shown in FIGS. 2A to 2C, namely, a worktable position shown in FIG. 2A, a scaffolding position shown in FIG. 2C, and a stored position shown in FIG. 2B. The different components and elements forming the locking mechanism 27 are shown in FIGS. 6-11 and are explained in full detail hereinafter.

In one preferred embodiment, the leg 3 initially locked into the stored position shown in FIG. 2B is first rotated to the scaffolding position shown in FIG. 2C and then to the worktable position shown in FIG. 2A. The leg 3 is then returned to the stored position as shown in FIG. 2B by rotating back the leg 3 over the scaffolding position as shown in FIG. 2C. It is understood by one of ordinary skill in the art that while one change between the different configurations is disclosed, other possible changes may be possible based on the inner workings of the locking mechanism 27.

FIG. 1 as an exploded view showing all of the main components of the worktable apparatus 1 as contemplated based of a first preferred embodiment. In this embodiment, two pairs of legs 3 are pivotally connected to both ends of the platform 2 and two locking mechanisms 27 are located on each end piece 33 between the legs. While a single embodiment is shown, one of ordinary skill in the art of worktable design understands that numerous possible combination of ends, legs, and geometries can be contemplated based on aesthetic and functional design characteristics and other relevant parameters. In the preferred embodiment, the scaffolding surface 5 is made of three panels 6, 7, 8 each shown respectively as FIGS. 16A to 16C. These panels are secured to the platform 2 using normal securing means. In the preferred embodiment, screws are used to secure the three panels 6, 7, 8 to the platform 2, but it is understood that the panels 6, 7, 8 can be locked in place with a lock plate, bolted, glued, molded into the platform, or even slid into position during assembly by any other normal fastening means. It is also understood by one of ordinary skill in the art that, while three different scaffolding panels 6, 7, 8 are shown and only one worktable surface 4 is illustrated, any number of possible functional configurations of panels may be used based on design requirements.

Figure 15:
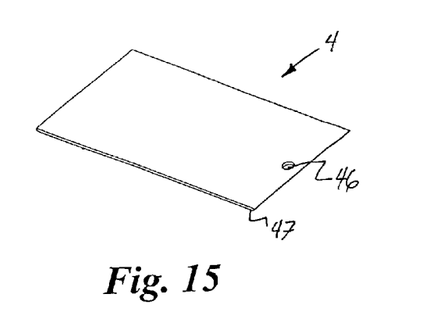
FIG. 15 is an isometric view of a possible embodiment of the worktable surface of the scaffolding and worktable apparatus according to an embodiment of the present disclosure.

FIG. 15 shows a detail view of the worktable surface 4 in a first possible embodiment. In one preferred embodiment, the worktable surface 4 is bolted to the platform 2 using bolts (not shown). What is also contemplated is a configuration where the worktable surface 4 is slid in the platform 2 during assembly and secured on the surface by two lateral C-shaped extrusions (not shown) along the length of the platform 2. It is understood by one of ordinary skill in the art that the worktable surface 4 can be secured to the platform 2 using any normal fastening means. As shown in FIG. 15, an opening 46 is made to allow the use of a drill on the worktable surface 4 and can also serves as a place where a holster of a power drill can be placed or can serve as an attachment for accessories. In the preferred embodiment, the worktable surface is made of a medium density fiber compound (MDF) with a sanded and sealed edge, but any normal material of sufficient mechanical resistance to withstand ordinary puncture and pressure when in position on the platform 2 may be used. In the embodiment shown in FIG. 1, a tray 9 is inserted in the plane of the worktable surface 4. The tray 9 includes a can holder 10, a pencil holder 11, and a series of smaller part holders 12. In the embodiment shown, a series of securing holes 13 is made in the tray 9 to allow the passage of screws to secure the tray 9 to the frame 2.

Figures 16A, 16B, 16C:
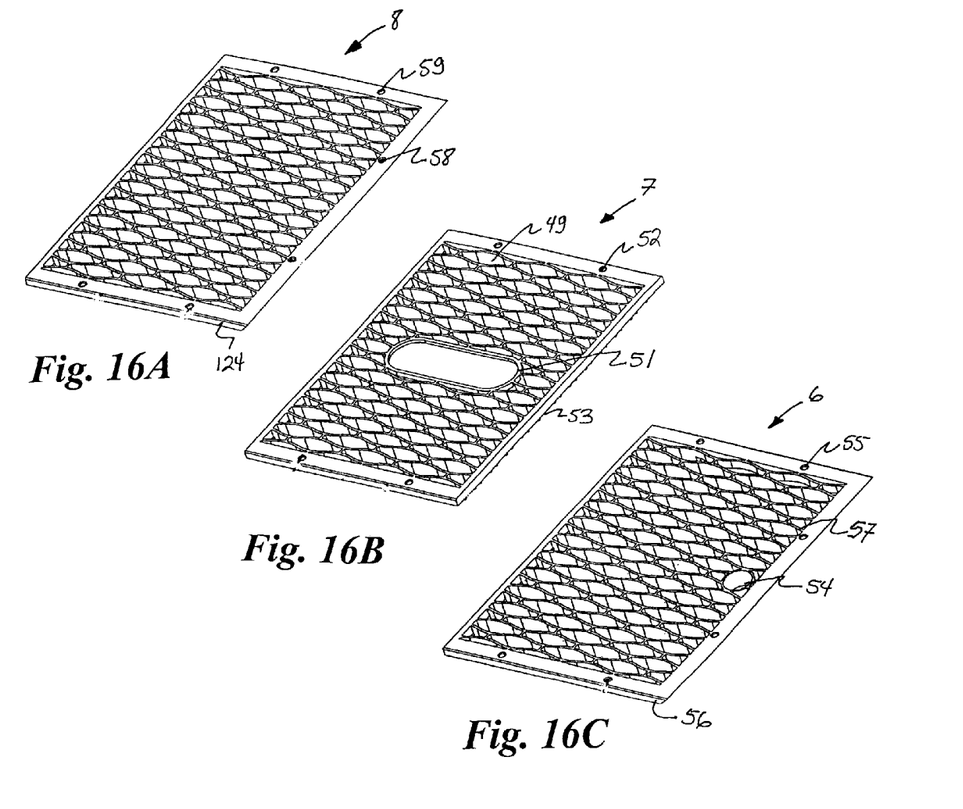
FIG. 16A is an isometric view of the center scaffolding panel of FIG. 1 according to an embodiment of the present disclosure.
FIG. 16B is an isometric view of the first side scaffolding panel of FIG. 1 according to an embodiment of the present disclosure.
FIG. 16C is an isometric view of the second side scaffolding panel of FIG. 1 according to an embodiment of the present disclosure.

FIGS. 16A to 16C show one possible embodiment of the three panels 6, 7, 8 forming the scaffolding surface 5. These three panels are shown in FIG. 16B with one possible surface rib-like pattern geometry 49 along the plane of the panels 6, 7, 8 in order to create a surface able to withstand pressure based on injection molded plastic technology. This ribbed surface is designed to optimize mechanical resistance for a minimum weight of low-density polymer. Each panel 6, 7, 8 is shown with a nominal wall 53 of 2.5 mm and an average panel thickness of 13.3 mm. In the preferred embodiment, polypropylene is used. In another embodiment, high-density polyethylene is used (HDPE) of orange color of PMS 1595C type is used. It is understood by one of ordinary skill in the art of scaffolding design that the surface must be able to resist normal wear and tear while possessing sufficient openings to allow for the normal flow of liquid through the surface and creating a surface where a foot or any other weight-producing element does not slip or move from its position.

In the preferred embodiment, the second panel 7 as shown in FIG. 16B is attached laterally by a series of side holes 52 able to allow the passage of a mechanical securing means, such as a bolt, to the platform 2. It is understood that, while only four side holes 52 are shown, any reasonable type, configuration, and quantity of holes sufficient to maintain the position of the second panel 7 relative to the platform 2 may be used. In addition, while no side holes are illustrated to attach the center panel 7 to the end panels 6, 8, it is understood that such attachments may be required based on the assembly technology. FIGS. 16A to 16C also show in a preferred embodiment tessellated cells of irregular shape 49, but it is understood that any possible shaped may be used.

FIG. 16C shows a similar panel 6 where only one hole 54 is found. While this hold can also serve to guide a user with the manipulation of the panel 6, it is understood that the location of the hole 54 is meant to be situated at the side of the platform 2 corresponding to the hole 46 made in the worktable surface 4. The correspondence of the hole 46 on one end of the platform 7 with the hole 54 on one end of the panel 6 allows a user to either secure several worktable apparatuses 1 into a stacked position by inserting a long object or, when the apparatus 1 is in use, to place a long object through both connecting holes to hold a tool in a vertical orientation. This hole 54 also allows for the use of a drill on the scaffolding surface 5, serves as a place where a holster of a power drill can be placed, or as an attachment for accessories. While it is understood by one of ordinary skill in the art that only two holes are shown in the panels 6, 7, 8, a very large quantity of possible functional configurations may be conceived. In addition, it is possible to use the empty space within the platform 2 in association with a specific design of the panels 6, 7, 8 and the worktable surface 4 for storage. Panels 6 and 8 each have a notch 56, 124, respectively, to help with the insertion of possible securing means, such as bolts through side holes 55, 59, respectively. FIG. 16A shows a series of longitudinal holes 58 used to secure the end of the panel 8 to the platform 2. The holes are also made in a section that includes an angled edge 125 designed for easy insertion in the platform 2. The panel 6 also is formed in its center region of ribs 57.

Figure 3A:
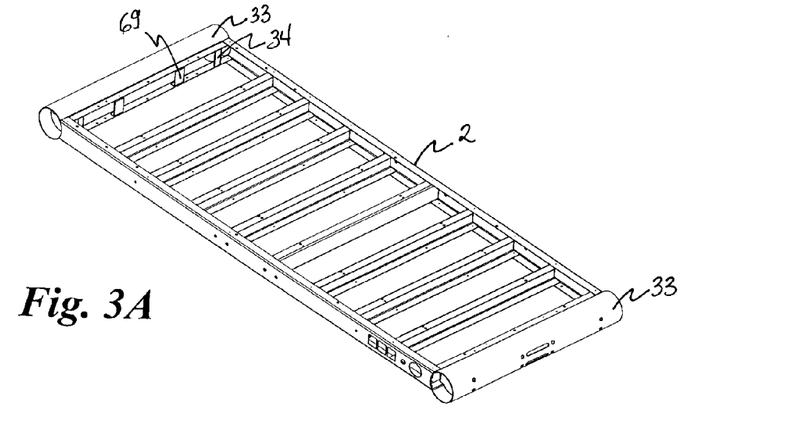
FIG. 3A is an assembled isometric view of the platform of FIG. 3B according to an embodiment of the present disclosure.
Figure 3B:
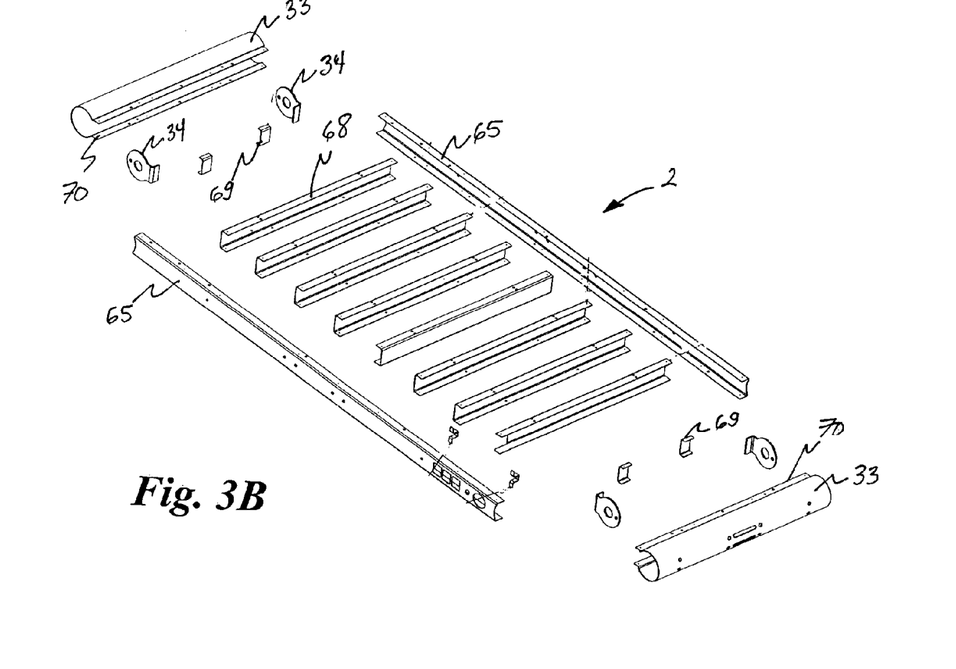
FIG. 3B is an exploded isometric view of the platform of the scaffolding and worktable apparatus according to an embodiment of the present disclosure.

Turning to FIGS. 3A to 3B, the platform 2 is designed to hold on one side the worktable surface 4 and on the other side the scaffolding surface 5. As shown in FIG. 1, a series of rigid elements are assembled in order to create the platform 2. A series of C-shaped elements 70 is attached at both ends of the platform 2 to contain a pivotal element 21 as shown in FIG. 1 and to hold the worktable surface 4, the tray 9, and the scaffolding panels 6, 7, 8 on the platform 2. The frame is also equipped with a series of holes designed to receive a power strip 19 as shown in detail in FIGS. 1 and 12. The platform 2 is made in a preferred embodiment of intermediate support beams 68 inserted between the frame front rails 65. Appropriate holes are drilled in the elements of the platform 2 to insure proper fixation. While the platform 2 in a first embodiment is made of a series of steel elements attached using classical means, such as bolts screws, or welding, the invention contemplates the use of a single, molded platform 2 or any other type of material, such as Kevlar or reinforced plastic with structural ribs, as long as sufficient mechanical characteristics can be maintained in the platform 2. A series of side support elements 69 is used to rigidify the end elements 70 while offering support for any locking mechanism 27 (not shown).

Figure 13:
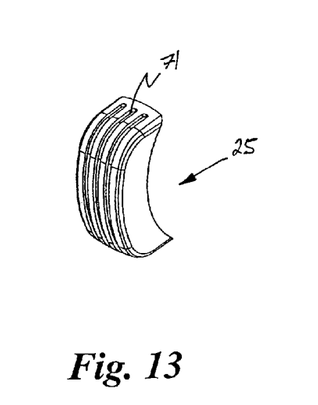
FIG. 13 is an isometric view of the end bumper of FIG. 1 according to an embodiment of the present disclosure.

FIG. 13 shows an embodiment of end bumpers 25 designed to be placed on the platform 2 to protect the end piece 33 and the end elements 70. In a preferred embodiment, the end bumpers 25 are injection molded using a rubberized substance capable of shock and deformation without damage. The end bumpers 25 are also designed to be of such height and thickness to protect the locking mechanism 27 from damage if the apparatus 1 is pushed against a flat wall. In the preferred embodiment, a series of grooves 71 are made in the external surface of the end bumpers 25 in order to reduce the effective weight of the bumpers 25 and increase the surface area while increasing overall surface friction. While a damage protection system is disclosed consisting of end bumpers 25, it is understood that the worktable apparatus 1 is to be used in a worksite environment prone to damages and bumps where a plurality of possible damage protection systems can be contemplated by one of ordinary skill in the art.

Figure 14:
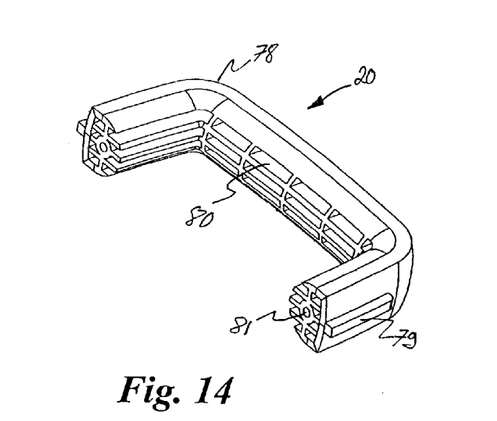
FIG. 14 is an isometric view of the handle of FIG. 1 according to an embodiment of the present disclosure.

FIG. 14 illustrates the handle 20 secured to both lateral sides of the platform 2 of the worktable apparatus 1 as shown in FIG. 1. The handle is attached to the platform 2 by a rigid mechanical means. In the preferred embodiment, an insert overmold covers the bolts with plastic. Lock washers and nuts (not shown) are then used to secure the handle 20 to the platform 2. In an alternate embodiment, screws (not shown) are used to secure the longitudinal elements 65 to the handles 20 via guiding holes 81, but it is understood by one of ordinary skill in the art that the handles 20 may be bolted to, fused to, slid into, locked onto, or inserted into to the worktable apparatus 1. It is also possible for the platform 2 to include the handles 20 as part of a one-piece molded design. The disclosed handles include a series of ribs 80 to reduce the weight of the handle without compromising the mechanical characteristic of the handles 20. In the preferred embodiment, external notches 79 are located on the external side of the handle 20, and the handle 20 includes semirounded corners 78. The external notches 79 serve to maintain legs 3 from compressing inwardly while the user is setting the worktable in the closed configuration 123 on the side. The notches 79 also serve to prevent rattling or wobbling of the legs 3. In one preferred embodiment, the legs 3 are locked by their foot 15 into the handle 20 on both sides of the worktable apparatus 1.

Figure 12:
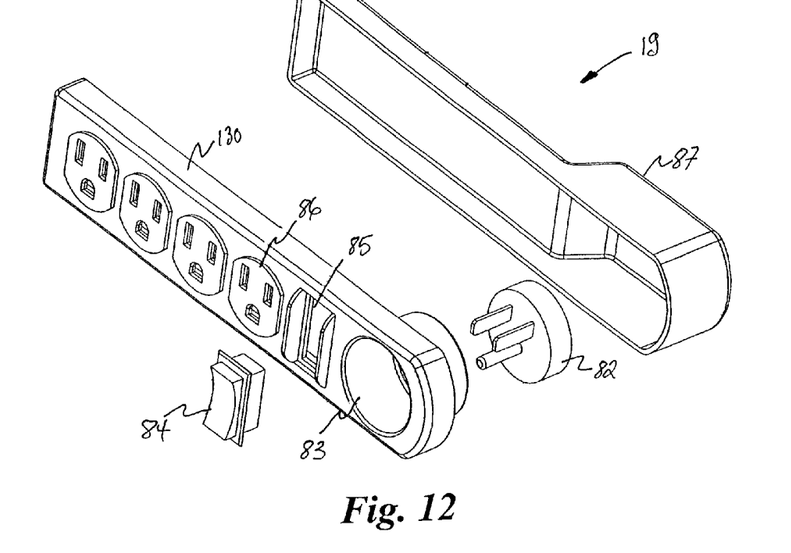
FIG. 12 is an exploded isometric view of the power strip of the scaffolding and worktable apparatus as shown in FIG. 1 according to an embodiment of the present disclosure.

FIG. 12 shows the power strip 19 as inserted into the platform 2. The power strip 19 as shown is a commonly found strip with a rear casing 87, a front casing 130, a power plug 82, a power hole 83, a current overload protection reset switch 84, a housing opening 85, and a plurality of outlets 86. In the preferred embodiment, the power plug 82 is functionally connected to the outlets 86. The use of a lighted switch is also contemplated. A user of the worktable apparatus 1 uses a power cord properly hooked into the local power network and inserts the power cord into the power plug 82. Once the switch 84 is open, the user is able to connect to the local power network by inserting one or several power cords into the outlets 86. For example, if the user of the worktable apparatus 1 must use a power drill and a power saw, he can insert the power plug of the drill into a first outlet 86 and the power plug of the saw into a second outlet 86. To activate the devices, the user needs to connect the power plug 82 to the local network and push the reset switch 84 if needed to turn on the power drill or the power saw. It is understood by one of ordinary skill in the art that, while no safety breaker is shown, the use of industrial tools on a worksite in association with construction design requirements may require the use of specific types of electrical devices and wiring. It is also understood that, while the power strip 19 is shown in the platform 2, it may be placed at any convenient location on the frame or in the legs 3.

In the preferred embodiment as shown in FIG. 1, four legs 3 are attached to the end pieces 33 of the platform 2 using pivots. In one embodiment, a step 88 is used to secure two legs 3 at the middle of their lengths using a step bracket 231 as shown in FIGS. 1 and 4A to 4C. FIG. 1 shows a step 88 made of a leg brace step 22 made of a hollow profile of generally rectangular shape, two end caps to close the leg brace step 22, and two step clips to fix the step 88 between two legs 3 on one side of the platform 2. What is also shown is the use of a set of support braces 17. While it is understood by one of ordinary skill in the art that a single leg brace step 88 is shown, each individual leg 3 may be secured to the platform using a leg brace 17 or a secondary support brace 202 attached from the leg 3 to the platform 2. FIGS. 2A to 2C show how the leg braces and the support braces may be attached to the legs 3 in such a way as to allow for the proper storage of the legs in the stored configuration as shown in FIG. 2B. FIGS. 5A to 5C show how the secondary support brace 202 is attached to the leg at 208 and to the platform 2 at 209. FIG. 5A is an exploded perspective view where a locking mechanism 205 is used to secure the secondary support brace 202 in either the open configuration shown in FIG. 5B or the closed configuration shown in FIG. 5C. In yet another embodiment, the legs brace 88 may be unassembled for shipping and reassembled by the user at the final destination.

Figures 4A, 4B:
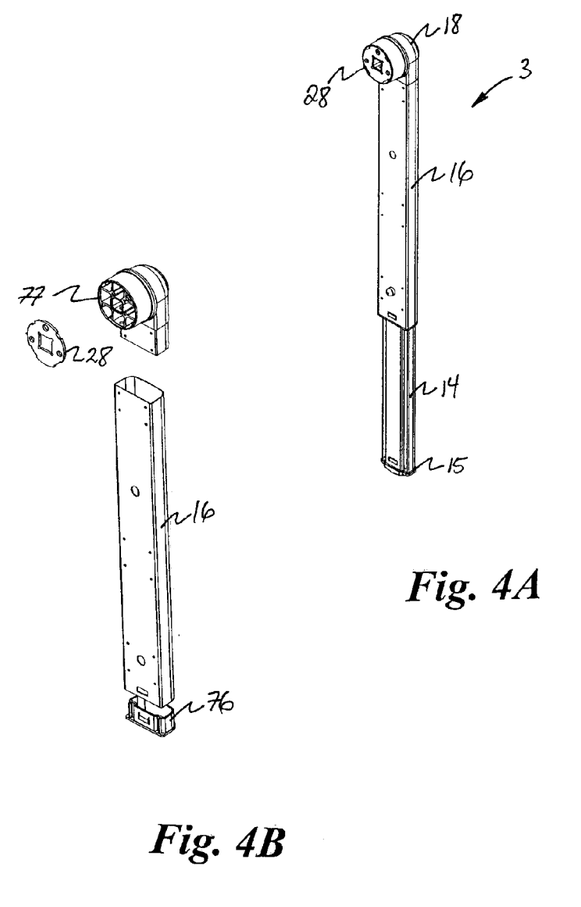
FIG. 4A is an assembled isometric view of the end leg of the scaffolding and worktable apparatus according to an embodiment of the present disclosure.
FIG. 4B is an exploded isometric view of the upper part of the end leg of the scaffolding and worktable apparatus as shown in FIG. 4A according to an embodiment of the present disclosure.
Figure 4C:
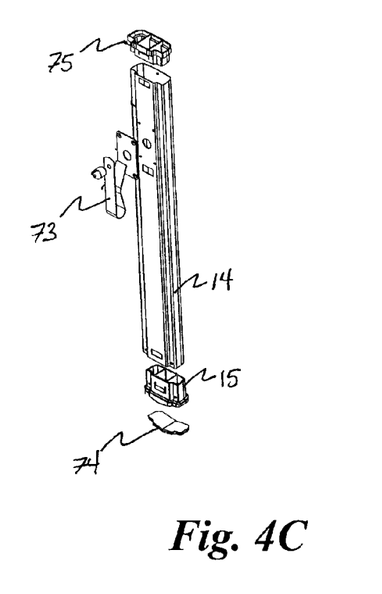
FIG. 4C is an exploded isometric view of the lower part of the end leg of the scaffolding and worktable apparatus as shown in FIG. 4A according to an embodiment of the present disclosure.
Figures 5A, 5B, 5C:
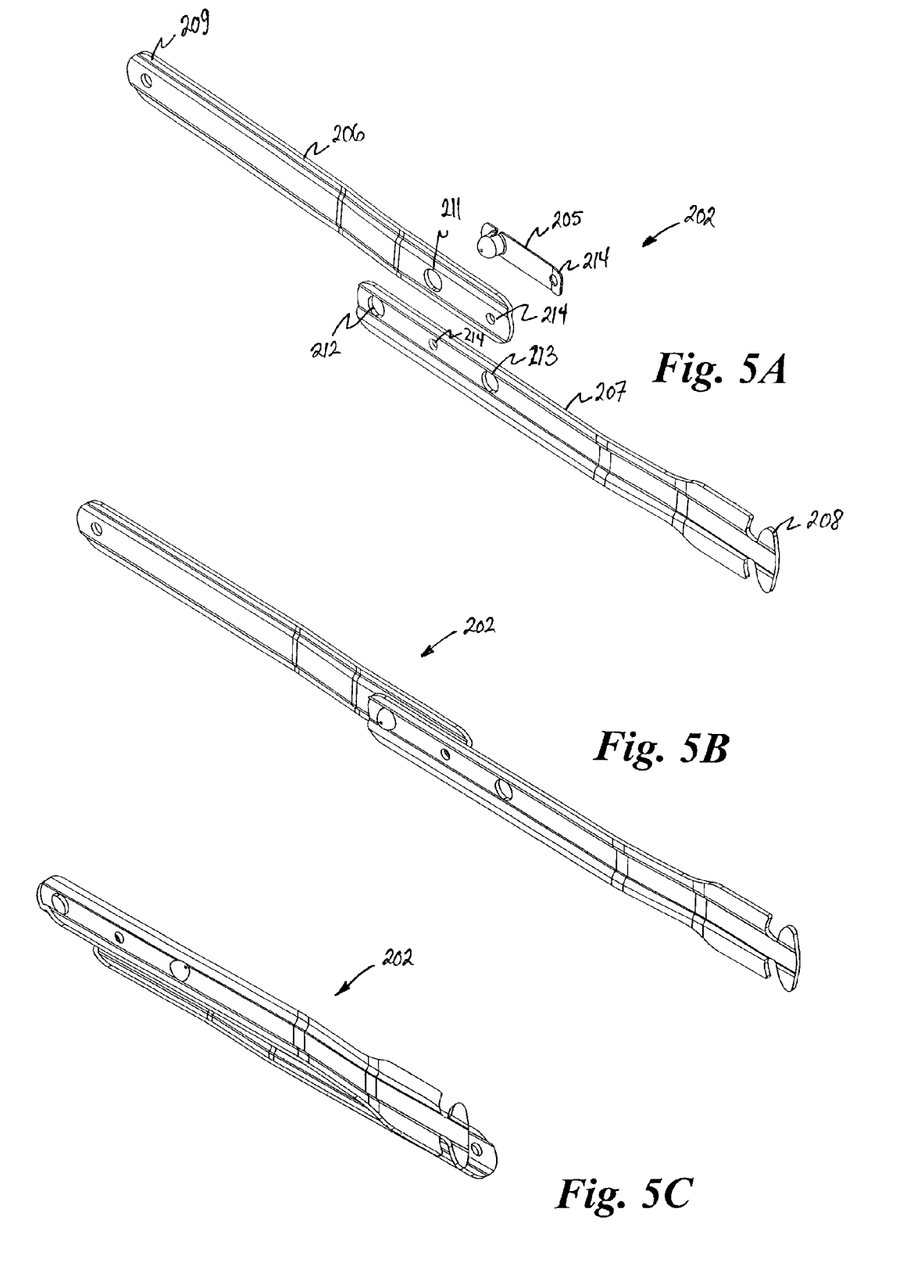
FIG. 5A is an exploded isometric view of the second support brace according to an embodiment of the present disclosure.
FIG. 5B is an isometric view of the second support brace of FIG. 5A in an open configuration such as the worktable configuration or the scaffolding configuration as shown in FIGS. 2A and 2C according to possible embodiments of the present disclosure.
FIG. 5C is an isometric view of the second support brace of FIG. 5A in a closed configuration such as the stored configuration as shown in FIG. 2B according to an embodiment of the present disclosure.
Figure 6:
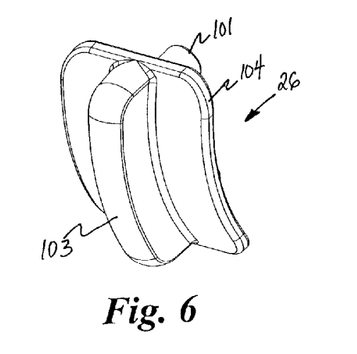
FIG. 6 is an isometric view of the locking slider of the locking mechanism of FIG. 1 along with other parts of the locking mechanism shown in FIGS. 7-11 according to an embodiment of the present disclosure.

FIGS. 4A to 4C show the different elements of the leg 3. The leg 3 is made of an upper leg 16 hollowed to contain the lower leg 14. A leg sleeve 76 is used to guide the lower leg 14 within the upper leg 16 and limit friction between the elements. The lower leg 14 is equipped with a foot 15 and a foot pad 74. The leg is designed to be light and maintain firm contact with the ground. The top section of the lower leg 14 is also equipped with a lower leg sleeve 75 in order to maintain the rigidity of the hollow tube of the lower leg 14. In one preferred embodiment, a snap button 73 is inserted in the lower leg 14 while a series of holes is made in the upper leg 16 to secure the lower leg at selected longitudinal positions along the leg 3. While a system with a snap button 73 and associated holes is shown, it is understood that a plurality of known systems for securing sliding legs at predetermined longitudinal positions may be used, such as rivets. The top end of the top leg 16 may be equipped with a corner section 18. The corner section allows for the insertion of the pivotal element 21 between two legs 3 within the end piece 33. In the disclosed illustration, the corner element 18 includes a rectangular section 77 secured to the corner element 18 by ribs, but it is understood that any mechanical system able to secure a pivotal element to the upper end of a leg 3 may be used. Both the first support brace 17 and the second support brace 202 as shown are secured to the upper leg 16 by a series of rivets 72, screws, or plastic fasteners. It is understood that while a rivet-based system is shown, any type of simple securing means commonly used to secure a small element to a closed profile may be used.

Figure 11:
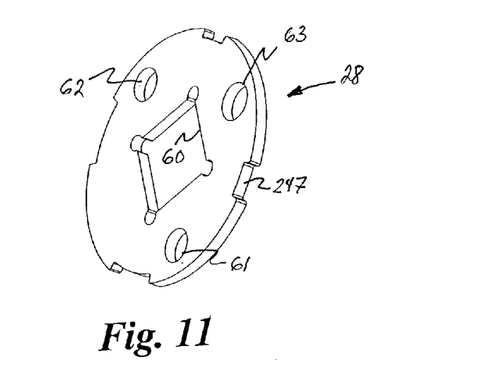
FIG. 11 is an isometric view of the leg connection plate as shown in FIG. 4B according to an embodiment of the present disclosure.

The legs can be rotated into the plane of the platform 2 in the stored configuration as shown in FIG. 2B. FIGS. 4A and 11 illustrate a leg connection plate 28. This leg connection plate 28 includes a center hole 60 made of the same geometry as the section of the pivotal element 21 as shown in FIG. 1. The leg connection plate 28 is inserted via four corners 247 into the corner elements 18 and pinned to the legs 3, but it is understood by one of ordinary skill in the art that if a cylindrical pivotal element 21 were used, a notch system or other fixation system to secure the pivotal element 21 to the leg connection plate 28 would be needed. The plate 28 in the preferred embodiment is made of steel and is 3 mm in thickness to prevent warping when shear or circumferential forces from a pin is made on the three pin holes 61, 62, 63. Each pin hole 61, 62, 63 corresponds to one possible locking position of the legs 3 with the locking mechanism 27 as disclosed hereafter. For example, if the worktable apparatus 1 is to be locked in the stored configuration as shown in FIG. 2B, the pin hole 61 may be used. The radial position of the pin holes 61, 62, 63 determines the angular locking position and orientation of the legs in the three possible positions. FIG. 1 discloses the pivotal element 21 to be inserted on both ends into the corner elements 18 of two different legs 3. In the preferred embodiment, the pivotal element 21 is a tube of square section 64 of 2 mm in thickness made of steel.

Figure 8:
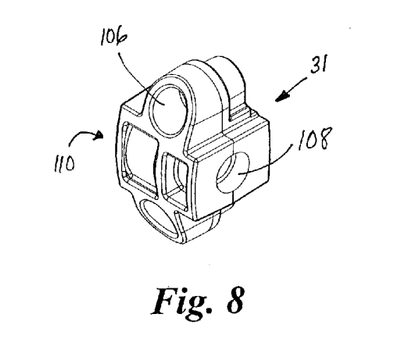
FIG. 8 is an isometric view of the shaft retainer of the locking mechanism of FIG. 1 according to an embodiment of the present disclosure.
Figure 9:
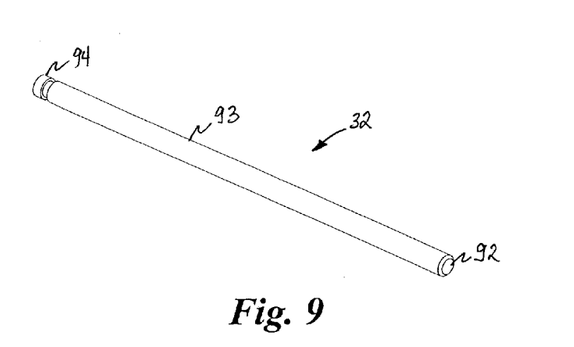
FIG. 9 is an isometric view of the locking pin of the locking mechanism according to an embodiment of the present disclosure.
Figure 10:
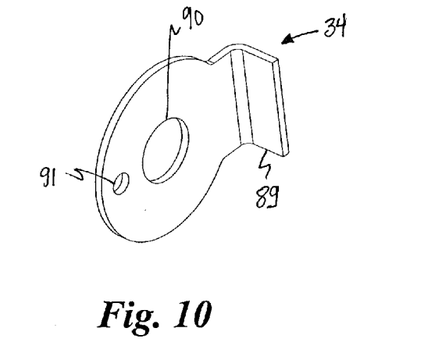
FIG. 10 is an isometric view of the leg locking plate of FIG. 3B according to an embodiment of the present disclosure.

Finally, the worktable apparatus 1 includes a locking mechanism for securing the at least one leg 3 into one of at least three positions as shown in FIGS. 2A to 2C. A leg locking plate 34 as shown in FIG. 10 is inserted within the end elements 70 as shown in FIG. 3B. The pivotal element 21 is then inserted within the hole 90 of the leg locking plate 34 of FIG. 10 equipped with a rounded section with a pin hole 91 and a flat portion 89 to be located next to the side support element 69 as shown in FIG. 3B. The leg locking plate 34 is designed to receive part of the locking mechanism and secure a locking pin 32 as shown in FIG. 9 through the appropriate locking retention mechanism. The leg locking plate 34 also allows for the locking pin 32 to be secured through one of the three pin holes 61, 62, 63 of the leg connection plate 28 shown in FIG. 11. The locking pin 32 as shown in FIG. 9 is made of a body section 93, a first end 94 with a groove is secured on the locking pin mechanism 31 as shown in FIG. 8, and a second end with a insertion angle 92 to be pushed in the locking plate 34 in one of the two locking retention mechanism. The locking pin 32 also includes a groove to prevent the pin from being pulled out of the shaft retainer 31.

Figure 7:
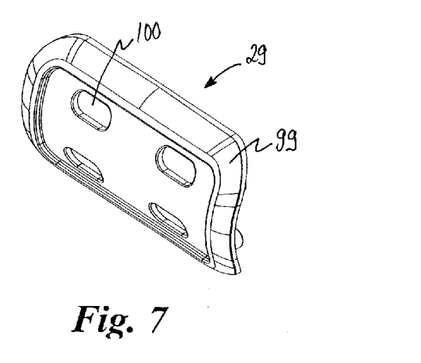
FIG. 7 is an isometric view of the locking cover of the locking mechanism of FIG. 1 according to an embodiment of the present disclosure.

The locking mechanism 27 is made of a locking cover 29 inserted on top of the end piece 33 at both ends of the platform 2 as shown in FIG. 1. The locking cover 29 is shown in FIG. 7. The locking cover 29 also includes a protection rim 99 a curved insert to help with mounting of the locking cover 29 on the end 33 and a series of holes to allow for the insertion and movement of the locking slider 26. It is understood that, while an embodiment of the locking cover 29 is shown in the locking mechanism 27, a very wide variety of possible locking mechanisms can be conceived. The locking slider 26 must move from an engaged position to a disengaged position by a fixed distance 100. The locking slider 26 of FIG. 6 also is equipped with a curve surface 104 to help engage with the curved surface of the locking cover 29. The locking slider 26 also has two locking feet 101 with foot holes 102 (not shown) for securing the locking slider 26 into the shaft retainer 31 into the locking holes 106 as shown in FIG. 8. In one embodiment, the shaft retainer 31 is mounted on the locking slider 26 and pinches the locking cover 29 in place between both parts. A series of bolts or screws can be used to fix the shaft retainer 31 to the locking slider 26.

The shaft retainer 31 as shown in detail in FIG. 8 is a single-molded part with several functional elements. The shaft retainer 31 is attached to the locking slider 26 via the top locking holes 106. The surface of the shaft retainer 31 is also curved 111 to mechanically connect with the curved surfaces 104, 97 of the locking slider 26 and the locking cover 29. On one side extremity of the shaft retainer 31, shown as 110, a hole allows for insertion of the locking pin 32. The pin 32 is also overmolded into the shaft retainer 31 to maintain the locking pin 32 in place.

Finally, because the worktable apparatus 1 is used in three possible positions illustrated in FIGS. 2A to 2C, it is understood that these possible positions are illustrative of an apparatus where a plurality of positions is disclosed. FIG. 2 shows a worktable where the worktable panel 4 and the tray 9 is located on the top section and the four legs are positioned forming an angle of approximately 90 degrees. In one embodiment disclosed, the angle 36 selected is 95 degrees from the horizontal, but it is understood by one of ordinary skill that any possible orientation to achieve the same purpose of placing the worktable panel 4 on the top of the worktable apparatus 1 is possible. In a second possible embodiment, the angle 36 shown in FIG. 2A and the angle 35 shown in FIG. 2A may be identical. FIG. 2A and FIG. 2C illustrate a preferred embodiment where the legs 3 are offset from vertical by 2 degrees 35 to create a small distance when folded in the stored configuration as shown in FIG. 2B. A small angle of 2 degrees is contemplated of the plane of the platform 2, it is understood by one of ordinary skill in the art that any angle resulting in a compact stored configuration as shown in FIG. 2B where the legs 3 do not touch the platform 2 may be used. In the scaffolding configuration shown in FIG. 2C, the angle of the legs with the plane made by the platform 2 is 101 degrees, or about 11 degrees from a right angle. In this embodiment, it is disclosed that the angle of the feet in the scaffolding configuration as shown in FIG. 2C is superior to the angle of the feet in the worktable configuration as shown in FIG. 2A. This is based on a design where more weight is placed on the worktable apparatus 1 in the scaffolding configuration. It is understood by one of ordinary skill in this art that, while a different set of angles has been selected, the determination of these angles are subject to variation based on the optimal force that may be placed upon the locking mechanism 27 and the legs 3.

The scaffolding and worktable apparatus 1 includes a platform 2 having a worktable surface 4, a scaffolding surface 5 in opposition, and an end of the platform 2 in contact with the worktable surface 4 and the scaffolding surface 5. The scaffolding and worktable apparatus comprises also least one first leg 3 pivotally connected to the end for pivoting between a stored position as shown in FIG. 2B, a scaffolding position as shown in FIG. 2C, and a worktable position as shown in FIG. 2A. The worktable apparatus 1 also includes a locking mechanism 27 for securing the at least one first leg 3 in the scaffolding position as shown in FIG. 2C and the worktable position as shown in FIG. 2A.

The platform 2 also comprises a second end in opposition in contact with the worktable surface 4 and the scaffolding surface 5 and at least one second leg 3 pivotally connected to the second end for pivoting between the stored position shown as FIG. 2B, the scaffolding position shown in FIG. 2C, and the worktable position shown in FIG. 2A. In an embodiment shown in FIG. 1, the two first legs 3 connect the first end at one extremity of the platform 2 and two second legs 3 connected to the opposite extremity of the platform 2. The first support braces 17 are connected at each opposed distal end to the two first legs 3 offset from the first pivoting end on the platform 2. The second support brace 202 is connected at a first distal end to one of the first legs 3 offset from the first pivoting end and at a second distal end to the platform 2. FIG. 1 shows a worktable 1 where two first support braces 17 are each respectively at the first and second end of the worktable and four second support braces 202 are attached to the two first and second legs 3 at the first distal end and at the second distal end to the platform 2. In one embodiment, the scaffolding and worktable apparatus 1 includes a first support brace 17 as a step adapted for supporting the foot of a user to facilitate the access of the scaffolding surface 5 to the user's foot.

In another embodiment, the worktable apparatus 1 includes a platform 2 with a periphery 200, a top surface and a bottom surface, wherein the top surface is a worktable 4, the bottom surface is a scaffolding surface 5, and a handle 20 is also connected to the periphery 200 between the top surface and the bottom surface. A leg 3 is also attached to the periphery 200 between the top surface and the bottom surface when the worktable apparatus 1 is in a storage position as shown in FIG. 2B. A locking mechanism 27 is attached to the periphery between the top surface and the bottom surface for securing the at least one first leg 3 in a scaffolding position shown in FIG. 2C or a worktable position shown in FIG. 2A.

While particular preferred embodiments have been shown and described, it is obvious to those skilled in the art that changes and modifications may be made without departing from the spirit and teaching of the disclosure. The matter set forth in the foregoing description and accompanying drawings is offered by way of illustration only and is not as intended as limitative. The actual scope of the disclosure is intended to be defined in the following claims when viewed in their proper perspective based on the related art.

What is claimed is:

1. A scaffolding and worktable apparatus, the apparatus comprising:
   a platform including a frame a frame, the frame having a pair of opposed longitudinal frame rails, a first generally tubular end piece and a second generally tubular end piece directly connected to respective ends of the frame rails, the frame rails and the end pieces defining four sides, a top surface and a bottom surface, the platform further including a worktable surface connected to the top surface of the frame and a scaffolding surface connected to the bottom surface of the frame; and
   a first leg assembly directly and pivotally connected to the first end piece and capable of pivoting between each of a stored position, where the first leg assembly is disposed parallel and adjacent to an exterior wall surface of the frame rails such that a major length of the first leg assembly extends from the first end piece and along the exterior wall surface, a scaffolding position, where the scaffolding surface is disposed above the worktable surface while the first leg assembly is supported on a ground surface, and a worktable position, where the worktable surface is disposed above the scaffolding surface while the first leg assembly is supported on the ground surface; and
   a second leg assembly directly and pivotally connected to the second end piece and capable of pivoting between each of the stored position, where the first and second leg assemblies are disposed parallel and adjacent to the exterior wall surface of the frame rails such that a major length of the second leg assembly extends from the second end piece and along the exterior wall surface, the scaffolding position, where the scaffolding surface is disposed above the worktable surface while the first and second leg assemblies are supported on the ground surface, and the worktable position, where the worktable surface is disposed above the scaffolding surface while the first and second leg assemblies are supported on the ground surface; and
   a locking mechanism disposed within the first end piece, the locking mechanism including a locking pin and a leg connecting plate, the locking pin oriented perpendicular to the frame rails and movable laterally to selectively engage holes in the leg connection plate for securing the first leg assembly in each of the stored position, the scaffolding position and the worktable position.

2. The scaffolding and worktable apparatus of claim 1, wherein the first leg assembly includes two first legs that each connect to one of a pair of opposing first openings of the first end piece and the second leg assembly includes two second legs that each connect to one of a pair of opposing second openings of the second end piece.

3. The scaffolding and worktable apparatus of claim 2, wherein a first support brace is connected to each of the two first legs at a position offset from the first end piece.

4. The scaffolding and worktable apparatus of claim 3, wherein a second support brace is connected to each of one of the second legs at a position offset from the second end piece.

5. The scaffolding and worktable apparatus of claim 3, wherein the first support brace is a step adapted for supporting a foot of a user when the apparatus is disposed in the scaffolding position to facilitate access of the scaffolding surface to the user's foot.

6. The scaffolding and worktable apparatus of claim 3, wherein the support brace contacts the worktable surface when the two first legs are disposed in the stored position.

7. The scaffolding and worktable apparatus of claim 1, wherein the platform further comprises a power strip integrated into the exterior wall surface of one of the frame rails.

8. The scaffolding and worktable apparatus of claim 1, further comprising a tray connected to the top surface of the frame and positioned adjacent the worktable surface.

9. The scaffolding and worktable apparatus of claim 8, wherein the tray includes a holder from a group consisting of a can holder, a pencil holder, and a part holder.

10. The scaffolding and worktable apparatus of claim 1, wherein the scaffolding surface includes a plurality of panels.

11. The scaffolding and worktable apparatus of claim 1, further comprising:
a handle connected to and extending from one of the frame rails.

* * * * *